(12) United States Patent
Cong et al.

(10) Patent No.: US 10,160,945 B2
(45) Date of Patent: Dec. 25, 2018

(54) HORIZONTAL IMMERSION COVER TYPE CARBON SUPPLEMENT DEVICE AND CARBON SUPPLEMENT METHOD USED FOR MICROALGAE CULTURE IN OPEN POND

(75) Inventors: Wei Cong, Beijing (CN); Ming Liu, Beijing (CN); Xia Wu, Beijing (CN); Shumei Wen, Beijing (CN); Dongmei Zhang, Beijing (CN); Zhongliang Sun, Beijing (CN)

(73) Assignee: Institute of Process Engineering, Chinese Academy of Sciences (CN)

( * ) Notice: Subject to any disclaimer, the term of this patent is extended or adjusted under 35 U.S.C. 154(b) by 471 days.

(21) Appl. No.: 14/396,597

(22) PCT Filed: May 7, 2012

(86) PCT No.: PCT/CN2012/075122
§ 371 (c)(1),
(2), (4) Date: Jan. 20, 2015

(87) PCT Pub. No.: WO2013/166638
PCT Pub. Date: Nov. 14, 2013

(65) Prior Publication Data
US 2015/0125946 A1    May 7, 2015

(51) Int. Cl.
*C12M 1/00* (2006.01)
(52) U.S. Cl.
CPC ............ *C12M 29/06* (2013.01); *C12M 21/02* (2013.01); *C12M 23/18* (2013.01); *C12M 23/38* (2013.01)

(58) Field of Classification Search
CPC ...................................................... C12M 21/02
See application file for complete search history.

(56) References Cited

U.S. PATENT DOCUMENTS

| 4,084,346 A | * | 4/1978 | Stengel | .................. | A01G 33/00 |
| | | | | | 435/257.1 |
| 2009/0068727 A1 | | 3/2009 | Karr | | |
| 2012/0034679 A1 | * | 2/2012 | Falber | .................... | A01G 33/00 |
| | | | | | 435/257.1 |

FOREIGN PATENT DOCUMENTS

| CN | 1982432 | 6/2007 |
| CN | 101519634 | 9/2009 |

(Continued)

*Primary Examiner* — Jonathan M Hurst
(74) *Attorney, Agent, or Firm* — Jack Schwartz & Associates, PLLC (57) ABSTRACT

The invention relates to the field of mass cultivation of microalgae and specifically relates to a horizontal submerged cover type carbon supplement device and carbon supplement method for cultivating microalgae in an open pond. The horizontal submerged cover type carbon supplement device for cultivating microalgae in an open pond, comprises: one or more than two covers and gas distributors, wherein the gas distributor is arranged at the bottom of the open pond and the cover is arranged above the gas distributor; the cover, in form of a cylinder with openings at both ends, is arranged along the flow direction of the culture solution, the two ends of the cover being a culture solution inlet and a culture solution outlet respectively; the gas distributor is kept away from the culture solution outlet of the cover by more than 40 cm. According to the invention, when microalgae cells are cultivated in the open pond, carbon dioxide can be effectively utilized for carbon supplement, so production cost is greatly reduced.

17 Claims, 4 Drawing Sheets

(56) References Cited

FOREIGN PATENT DOCUMENTS

| WO | WO2009/149519 | 12/2009 |
|----|---------------|---------|
| WO | WO2011/058267 | 5/2011  |

\* cited by examiner

Fig. 12

HORIZONTAL IMMERSION COVER TYPE CARBON SUPPLEMENT DEVICE AND CARBON SUPPLEMENT METHOD USED FOR MICROALGAE CULTURE IN OPEN POND

FIELD OF THE INVENTION

The invention relates to the field of mass cultivation of microalgae and specifically relates to a horizontal submerged cover type carbon supplement device and carbon supplement method for cultivating microalgae in an open pond.

BACKGROUND OF THE INVENTION

Microalgae can produce a variety of chemical products by fixing carbon dioxide through photosynthesis. Some microalgae can produce aliphatic hydrocarbons, for example, the hydrocarbon production of botryococcus can reach 15%-75% of dry cell weight; some microalgae can accumulate glycogen; some microalgae can accumulate glycerol, wherein the lipid content of many microalgae can reach 60% or above of the dry cell weight. The average combustion heat of fuel oil obtained by pyrolysis of algae biomass can be up to 33 MJ/kg. Microalgae can be cultured in seawater, salty water or semi-salty water, avoiding scrambling for land and freshwater resources with crops, and can be cultured with waste water. So, microalgae could be an important source to obtain biological resources in regions lack of freshwater or with barren land. Therefore microalgae are expected to be important sources for future energy and chemical products.

The carbon in microalgae cells accounts for more than a half of the dry cell weight of the cells, and the algae cells can fix carbon dioxide as their own components through photosynthesis in growing process, so that the supply of carbon sources should be assured in the culture medium in the algae culture process. The inorganic carbon sources in the algae culture medium exist in three forms, namely $HCO_3^-$, $CO_3^{2-}$ and free $CO_2$. The ratio of the three forms of carbon sources in water varies with the pH value of the culture medium. If $NaHCO_3$ is used as the carbon source, with the dissociation of $HCO_3^-$ and the utilization of $CO_2$, the pH value of the culture medium rises continually, more than half of the added $NaHCO_3$ is converted to $Na_2CO_3$ which could not be utilized by algae, resulting a waste and considerable consumption of carbon source; moreover, the medium is difficult to be recycled because of the rise of its pH value. If $CO_2$ is used as the carbon source, which is directly utilized by the microalgae, then the problem that the pH value of the culture medium rises can be avoided, which is beneficial for maintaining an desirable culture environment and allows the medium to be used repeatedly or for an extended period.

Cultivation in an open pond is a traditional and simple mode of microalgae culture, and is also recognized as a mature microalgae culture technology currently. It has the advantages of having a simple construction and being easy to operate, and has been applied to commercial production of *spirulina*, *chlorella* and *Dunaliella salina* (Chaumont D., J. Appl. Phycol., 1993, 5:593-604; Richmond A., Progress in Physiological Research, Vol. 7, Biopress, Bristol., 1990, 269-330; Borowitzka Bioresource Technology, 1991, 38: 251-252). However, the depth of the culture solution in a traditional open pond is usually kept at 20-30 cm, if the $CO_2$ is directly aerated into the open pond in a bubbling way, due to the very short residence time of the bubbles in the culture solution, the absorption efficiency of the $CO_2$ is very low—only 13%-20% of the $CO_2$ is absorbed (Becker E W, Microalgae: biotechnology and microbiology, Cambridge University Press, Cambridge, 1994, pp 293).

Ferreira et al. (Ferreira B S, Fernandes H L, Reis A and Mateus M. Microporous hollow fibers for carbon dioxide absorption: mass transfer model fitting and the supplying of carbon dioxide to microalgae cultures. Journal of Chemical Technology and Biotechnology, 1998, 71: 61-70) utilized a hollow fiber membrane to enhance gas-liquid mass transfer, so as to improve the absorption efficiency of the $CO_2$, but the method is high in cost, and the hollow fiber membrane is prone to be fouled.

As for the method of L I Yeguang, H U Hongjun, ZHANG Liangjun and CHEN Zhixiang (Study on $CO_2$ supply technique for *spirulina* production, Journal of Wuhan Botanical Research, 1996, 14 (4): 349-356), a gas-cover in size of several square meters is arranged on the surface of microalgae culture solution, and carbon dioxide gas is introduced into the gas-cover, so that the carbon dioxide is transferred into the culture solution through the water surface shrouded by the cover. The problems with this method are as follows: the specific interfacial area for gas-liquid exchange is small; the mass transfer rate is lowered down due to accumulation of oxygen and nitrogen in the gas-cover, and the oxygen and nitrogen need to be ventilated frequently, so part of the carbon dioxide in the gas-cover is wasted; for a gas source containing low-content carbon dioxide, the absorption efficiency of the carbon dioxide is very low; when the pressure in the gas-cover is slightly higher, the gas may leak out from the edge of the gas-cover through the liquid surface outside the gas-cover. Groove type carbon supplement method (CN200610018771.9, Device for Supplementing Carbon Dioxide into Microalgae Cultivation Pond) is as follows: a deep groove is dug and located beside a culture pond to enable the culture solution to flow through the deep groove, a gas sparger is arranged at the bottom of the groove, through which the carbon dioxide is supplied into the culture solution. The method may disrupt the spatial layout of the traditional open pond; and furthermore, the culture solution in the groove is not mixed well, the bottom of the groove becomes a dead zone for mass transfer after being saturated with carbon dioxide after a period of sparging, and then the deep groove does not function as a mass exchanger.

CONG Wei et al. (CN200510126465.2, Carbon Supply Device for Large-scale Culture of Microalgae and its Application and Use) develop a trap type carbon supplement device for directly supplementing $CO_2$ into the culture solution in an open pond, wherein the culture solution can form a circulation in the trap type carbon supplement device, thereby the time for gas-liquid contact is greatly prolonged; moreover, gas is supplied from the bottom of the trap type carbon supplement device; so that the absorption efficiency of $CO_2$ is greatly improved. However, the carbon supplement device increases the flow resistance in the open pond, thereby resulting in increased electrical energy consumption for driving the fluid with a paddle wheel under the same flow velocity, and relatively more construction workload.

SUMMARY OF THE INVENTION

An objective of the invention is to provide a horizontal submerged cover type carbon supplement device for cultivating microalgae in an open pond, for solving the above problems.

Another objective of the invention is to provide a carbon supplement method for cultivating microalgae in an open pond.

The general technical solution of the invention is as follows: a gas distributor is arranged at the bottom of the open pond, above which a cover submerged in the culture solution and extends sufficiently along the flow direction of the culture solution is arranged, thereby the bubbles of the gas are sealed within the cover and have sufficient gas-liquid contact time when the bubbles flow along with the culture solution within the cover, thus the absorption efficiency of the gas is improved.

The horizontal submerged cover type carbon supplement device for cultivating microalgae in an open pond of the invention comprises one or more than two covers 1 and gas distributors 2, wherein the gas distributor 2 is arranged at the bottom of the open pond and the cover 1 is arranged above the gas distributor 2, the cover 1, in form of a cylinder with openings at both ends, is arranged along the flow direction of the culture solution, the two ends of the cover 1 being a culture solution inlet 3 and a culture solution outlet 4 respectively; moreover, the gas distributor 2 is kept away from the culture solution outlet 4 of the cover 1 by more than 40 cm.

Alternatively, the gas distributor 2 can be positioned below the culture solution inlet 3 of the cover 1 or other parts of the cover as long as the distance from the gas distributor 2 to the culture solution outlet 4 of the cover 1 is more than 40 cm. Preferably, the gas distributor 2 is positioned below the culture solution inlet 3 of the cover 1.

According to the carbon supplement device of the invention, preferably, the distance from the gas distributor 2 to the culture solution outlet 4 is 60-750 cm. In order to facilitate construction and ensure sufficient carbon dioxide absorption efficiency, the length of the cover 1 along the flow direction of the culture solution should guarantee the gas-liquid contact time being 3 s-15 s, therefore, preferably, the distance from the gas distributor 2 to the culture solution outlet 4 of the cover 1 is the distance for the culture solution to flow in the open pond within 3 s-15 s. Generally, the flow velocity of the culture solution in an open pond is 20-50 cm/s, therefore, preferably, the distance from the gas distributor 2 to the culture solution outlet 4 of the cover 1 is 60-750 cm.

According to the carbon supplement device of the invention, wherein the cover 1 is directly mounted at the bottom of the open pond or overhead arranged at the bottom of the open pond.

According to the carbon supplement device of the invention, wherein the bottom of the cover 1 can be open or closed.

According to the carbon supplement device of the invention, wherein the body of the cover 1 is a semi-circular cylinder, an arc-shaped cylinder, a rectangular cylinder or a trapezoidal cylinder.

According to the carbon supplement device of the invention, in order to reduce the flow resistance of the fluid in the cover 1, the culture solution inlet 3 and/or the culture solution outlet 4 of the cover 1 can be in a structure with a bell mouth.

According to the carbon supplement device of the invention, wherein the height of the cover 1 is 2-20 cm and shall be determined so as to be submerged by the culture solution.

According to the carbon supplement device of the invention, wherein the width of the cover 1 is larger than or equal to 2 cm. The width of each cover 1 can be as small as 2 cm (i.e., covering one gas distribution pipe), and be as large as the width of the open pond channel (i.e., covering a plurality of gas distribution pipes or gas distributors).

According to the carbon supplement device of the invention, the gas spreading surface (plate) of the gas distributor can be made of porous materials, and the gas distributor can be a pipe-like gas distributor or a gas distributor composed of one or more gas sparging heads connected to a gas delivering pipe. The gas distributor can be hard, such as a porous ceramic pipe or a glass sand core, or be soft, such as a commercially available aeration hose or a variable-pore aeration hose.

According to the carbon supplement device of the invention, wherein conjoining processing can be performed on more than two of the covers 1 to form a conjoined structure.

The wall thickness of the cover 1 is 1 mm-10 mm.

The material of the cover can be transparent or opaque, such as a plastic sheet, a stainless steel sheet, a wood sheet and other materials, which can be processed and shaped to have certain strength.

According to the carbon supplement method for cultivating microalgae in an open pond based on the carbon supplement device of the invention, the horizontal submerged cover type carbon supplement device is arranged at the bottom of the open pond along the direction of the channel of the open pond to enable the culture solution to inundate the top of the cover 1; the culture solution flows into the culture solution inlet 3 of the cover 1 under the driving of a stirrer 9 of the open pond and flows out of the culture solution outlet 4 of the cover 1 after being in contact with $CO_2$ released from the gas distributor in the carbon supplement device.

The flow velocity of the culture solution in the open pond is 20-50 cm/s.

The flow rate of the $CO_2$ in the horizontal submerged type carbon supplement device, calculated as pure $CO_2$ under standard condition, is 0.1-20 L/min per meter of the width of the open pond.

The flow of the culture solution in the open pond can be implemented by the driving of a stirrer of the open pond, such as a paddle wheel or a rotating arm, and the stirrer can be made of bamboo chips, plastics, stainless steel, other metal materials and the like.

The depth of the culture solution in the open pond can be 2-30 cm.

According to the carbon supplement method of the invention, when the depth of the culture solution in the open pond is relatively small, the stirrer of the open pond can be lowered to the position where the blade tip of the stirrer is lower than the bottom of the open pond, namely the blade tip of the stirrer 9 is lower than the bottom of the open pond.

According to the carbon supplement method of the invention, when the depth of the culture solution in the open pond is relatively small, a shallow groove can be dug out in the region at the bottom of the open pond where the carbon supplement device is to be placed so as to install the carbon supplement device, that is to say, the carbon supplement device is installed in a position which is lower than the bottom of the open pond.

The bottom of the shallow groove for placing the carbon supplement device can be a flat bottom, a flat bottom with round corners or a semi-circular bottom; and the material of the bottom of the shallow groove can be cement, a plastic plate, a stainless steel plate, bricks, the same material as that of the bottom of the open pond or the like.

When the gas distributor has a long shape, preferably, the gas distributor is arranged in such a way that the length direction of the gas distributor is consistent with the flow direction of the culture solution.

According to the carbon supplement method of the invention, wherein the $CO_2$ is one or more of cleaned flue gas, industrial $CO_2$ gas, pure $CO_2$ gas or air mixed with $CO_2$, or liquid $CO_2$.

The medium for cultivating microalgae can be any known medium which is suitable for microalgae growth in the art, such as Zarrouk medium, SM medium, $ASP_2$ medium, BG-11 medium and the like, and can also be a medium which is specially needed for a certain alga or a medium which needs $CO_2$ in the culture process.

The horizontal submerged cover type carbon supplement device and carbon supplement method of the invention can be used for supplementing $CO_2$ in large-scale culture process of various microalgae in an open pond, including *spirulina, scenedesmus, haematococcus pluvialis, Dunaliella salina, chlorella, chlamydomonas* and other various microalgae.

During the microalgae culturing process in an open pond, when $CO_2$ is used for carbon source, the reason for the extreme low utilization of the carbon source is due to the fact that the culture solution layer is relatively shallow and so the gas-liquid contact time is short, thus the $CO_2$ gas overflows without being absorbed sufficiently. The carbon supplement device of the invention can not only overcome the above shortcomings, but also realize higher absorption efficiency in comparison with the gas-cover method of L I Yeguang, H U Hongjun, ZHANG Liangjun and CHEN Zhixiang (Study on $CO_2$ supply technique for *spirulina* production. Journal of Wuhan Botanical Research, 1996, 14 (4): 349-356), are more convenient in operation in comparison with the groove type carbon supplement (patent CN200610018771.9), and reduce the flow resistance of fluid and save energy in comparison with the trap type carbon supplement device (patent CN200510126465.2). According to the invention, when microalgae cells are cultivated in an open pond, the carbon dioxide can be efficiently utilized as carbon source, and so the production cost is greatly reduced.

DESCRIPTION OF THE REFERENCE NUMERALS

| | |
|---|---|
| 1. | Cover |
| 2. | Gas distributor |
| 3. | Culture solution inlet |
| 4. | Culture solution outlet |
| 5. | Flow direction of culture solution |
| 6. | Bottom of an open pond |
| 7. | Wall of an open pond |
| 8. | Surface of microalgae culture solution |
| 9. | Stirrer |
| 10. | Arc-shaped groove |
| 11. | Shallow groove |
| 12. | pH sensor |
| 13. | Control device |
| 14. | $CO_2$ gas source |
| 15. | Execution mechanism |
| 16. | Flow meter |
| 17. | Pressure gauge |

DETAILED DESCRIPTION OF THE INVENTION

Figure 1:
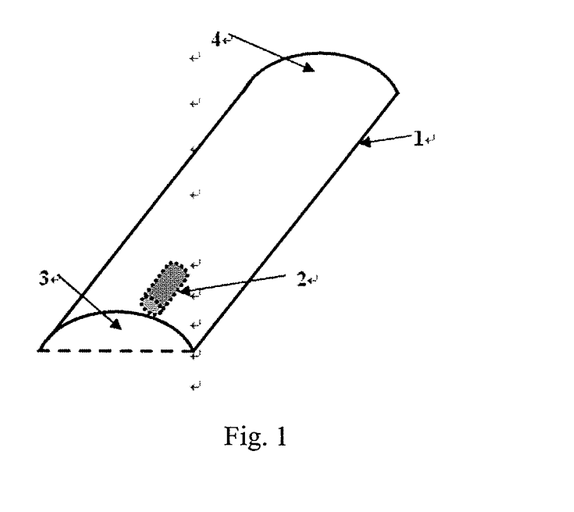
FIG. 1 is a schematic diagram of a horizontal submerged cover type carbon supplement device for cultivating microalgae in an open pond of the invention.
Figure 2:
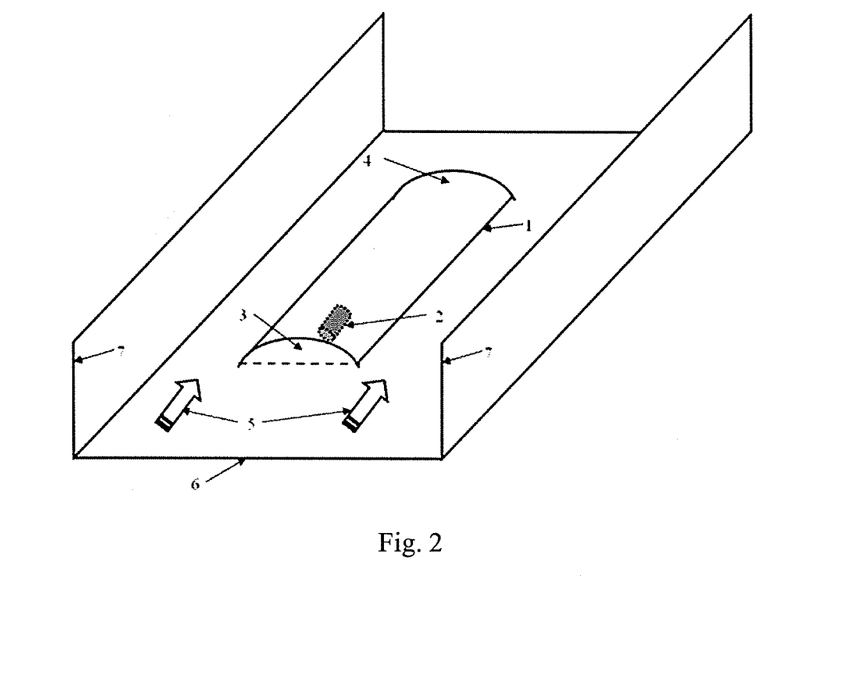
FIG. 2 is a schematic diagram of the location of the horizontal submerged cover type carbon supplement device in the channel of an open pond for cultivating microalgae in an open pond of the invention
Figure 3:
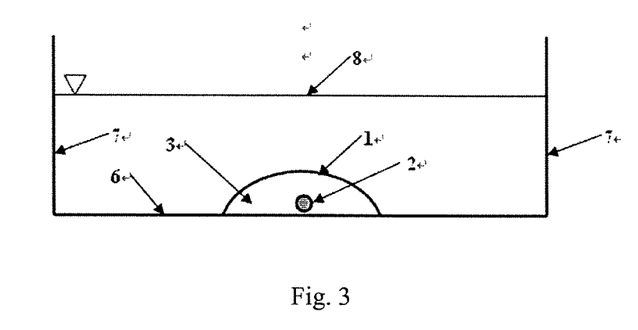
FIG. 3 is a view of the horizontal submerged cover type carbon supplement device in use along the flow direction of culture solution for cultivating microalgae in an open pond of the invention.
Figure 4:
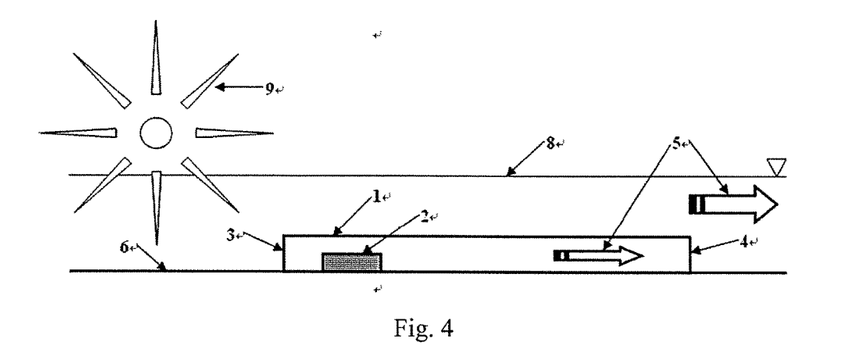
FIG. 4 is a side view of the horizontal submerged cover type carbon supplement device in use for cultivating microalgae in an open pond of the invention.
Figure 5:
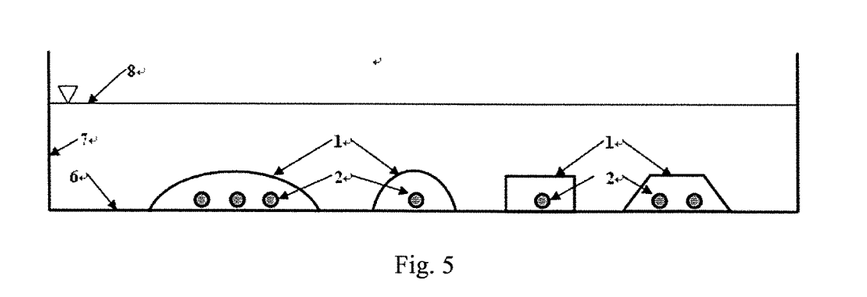
FIG. 5 is a schematic diagram of different cross section shapes of the main body of a cover 1 of the carbon supplement device of the invention (showing the covers which are directly located at the bottom of the open pond, showing one or more gas distributors below each cover and showing the section shapes of the covers).
Figure 6:
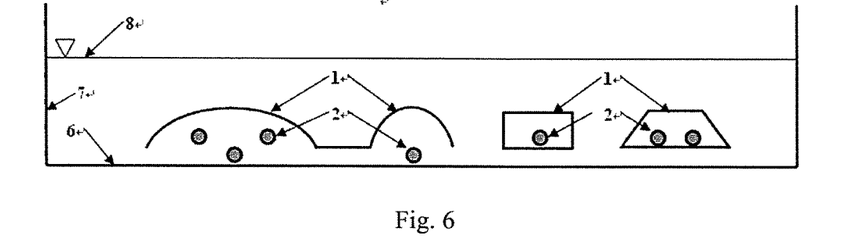
FIG. 6 is a schematic diagram of different arrangement ways of the carbon supplement device of the invention (showing overhead covers, showing covers with open or closed bottoms, showing conjoined covers and showing grounded or overhead gas distributors).
Figure 7:
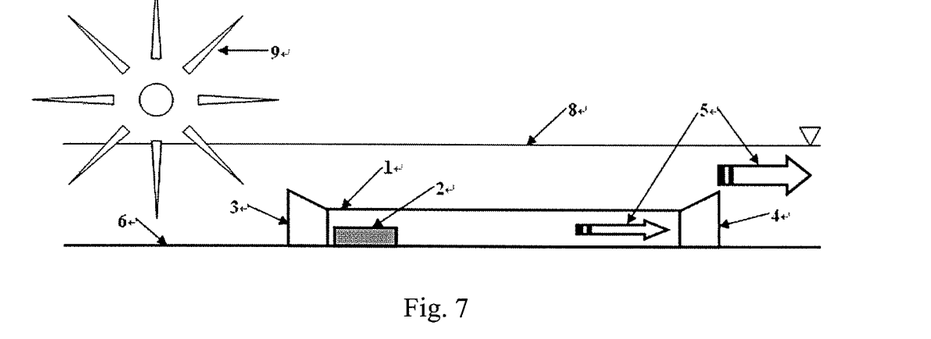
FIG. 7 is a schematic diagram of the carbon supplement device of the invention, the cover of which is in a structure with a bell mouth.

A horizontal submerged cover type carbon supplement device for cultivating microalgae in an open pond of the invention comprises one or more than two covers 1 and gas distributors 2 (FIG. 1 and FIG. 6), wherein the gas distributor 2 is arranged at the bottom 6 of the open pond, the cover 1, covering the gas distributor 2, takes the form of a cylinder with openings at both ends and is arranged along the flow direction 5 of the culture solution, with the two ends being a culture solution inlet 3 and a culture solution outlet 4 (FIG. 2 and FIG. 3) respectively; moreover, the gas distributor 2 is kept away from the culture solution outlet 4 of the cover 1 by more than 40 cm. Preferably, the gas distributor 2 is kept away from the culture solution outlet 4 of the cover 1 by 60-750 cm. The cover 1 can be directly mounted at the bottom of the open pond (FIG. 5) or overhead arranged at the bottom of the open pond (FIG. 6, a supporting device is omitted), with the bottom of the cover 1 being open or closed (FIG. 6). The main body of the cover 1 can be a semi-circular cylinder, an arc-shaped cylinder, a rectangular cylinder or a trapezoidal cylinder (FIG. 5). In order to reduce the flow resistance of the fluid in the cover, the culture solution inlet 3 and/or the culture solution outlet 4 of the cover 1 can be in a structure with a bell mouth (FIG. 7). The height of the cover 1 is 2-20 cm, which is determined so as for the cover 1 to be submerged by the liquid surface 8 of the microalgae culture solution. The width of the cover 1 can be as small as 2 cm (i.e. covering one gas distribution pipe), and be as large as the width of the open pond channel (namely the distance between the walls 7 of the open pond on the two sides of the flow channel) (i.e. covering a plurality of gas distribution pipes or gas distributors). Two or more covers 1 can be formed into a conjoined structure by conjoining processing (FIG. 6).

Figure 11:
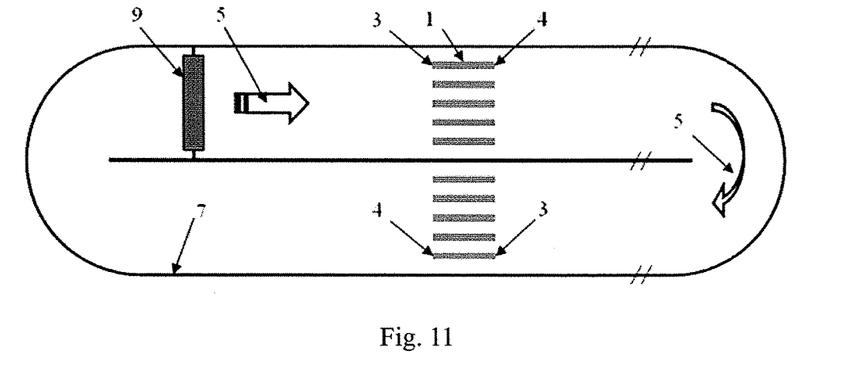
FIG. 11 is a schematic diagram of overall layout of the carbon supplement device for cultivating microalgae in an open pond of the invention (top view).

In a carbon supplement method for cultivating microalgae in an open pond of the invention, one or more groups of horizontal submerged cover type carbon supplement devices are arranged in the open pond along the direction of the flow channel, each group comprises one or more horizontal submerged cover type carbon supplement devices, and each horizontal submerged cover type carbon supplement device comprises one cover along the flow direction of the culture solution and one or more gas distributors shrouded by the cover. Preferably, the gas distributors are positioned at the culture solution inlet 3 of the cover. The overall layout is shown in FIG. 11, wherein the number of groups of the horizontal submerged cover type carbon supplement devices, the number of the horizontal submerged cover type carbon supplement devices in each group and the number of the gas distributors below each cover are determined according to the carbon supplementing flow rate of a single horizontal submerged cover type carbon supplement device, the size of the open pond, the growth rate of objective microalgae to be cultured and the requirements of culture conditions. When the culture solution flows in the open pond under the driving action of a stirrer (conventional stirrer in the art is a paddle wheel), part of the culture solution flows into the horizontal submerged cover type carbon supplement device from the culture solution inlet 3 so as to be in contact with the gas containing carbon dioxide, which is released from the gas distributor and sealed below the cover, then the culture solution flows through the space below the cover and flows out of the horizontal submerged cover type carbon supplement device from the culture solution outlet 4, so that the gas-liquid contact time is greatly prolonged; and on the other hand, after the gas containing carbon dioxide passes through the gas distributor, the gas becomes into very small bubbles, which makes the gas-liquid contact interfacial area is drastically increased, thereby the absorption efficiency of the carbon dioxide is greatly improved.

The flow of the culture solution can be implemented by the driving of a stirrer of the open pond, such as a paddle wheel or a rotating arm, and the stirrer can be made of bamboo chips, plastics, stainless steel, other metal materials and the like.

When the horizontal submerged cover type carbon supplement device is used, the flow velocity of the culture solution in the open pond is 20-50 cm/s generally, and the flow rate of $CO_2$ (calculated as pure $CO_2$ under standard conditions) is 0.1-20 L/min per meter of the width of the open pond.

The depth of the culture solution in the open pond can be 2-30 cm.

Figure 8:
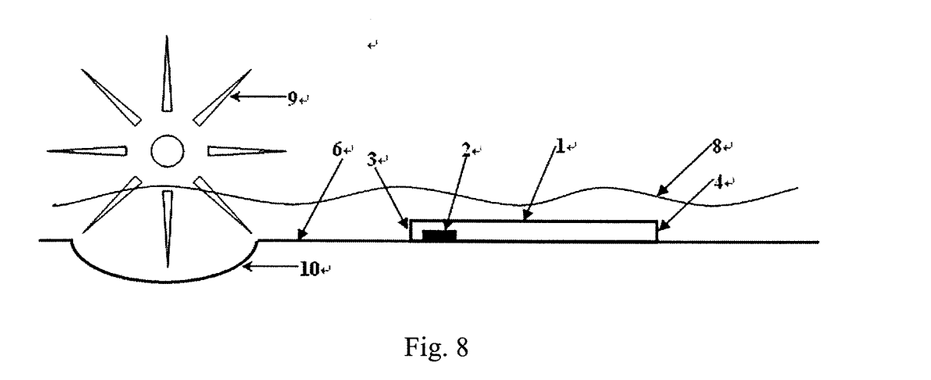
FIG. 8 is a schematic diagram of the carbon supplement device of the invention, which is used together with a stirrer of which the blade tip is lower than the bottom of the open pond when the depth of the culture solution is relatively small.
Figure 9:
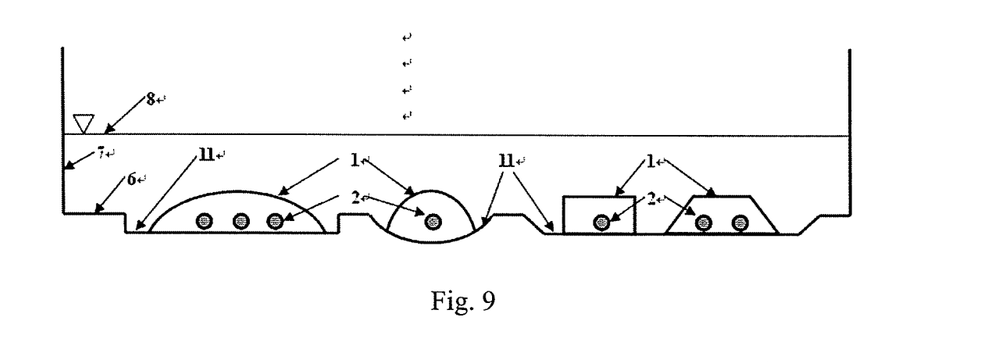
FIG. 9 is a view of the carbon supplement device of the invention, which is mounted in a position lower than the bottom of the open pond, along the flow direction of the culture solution.
Figure 10:
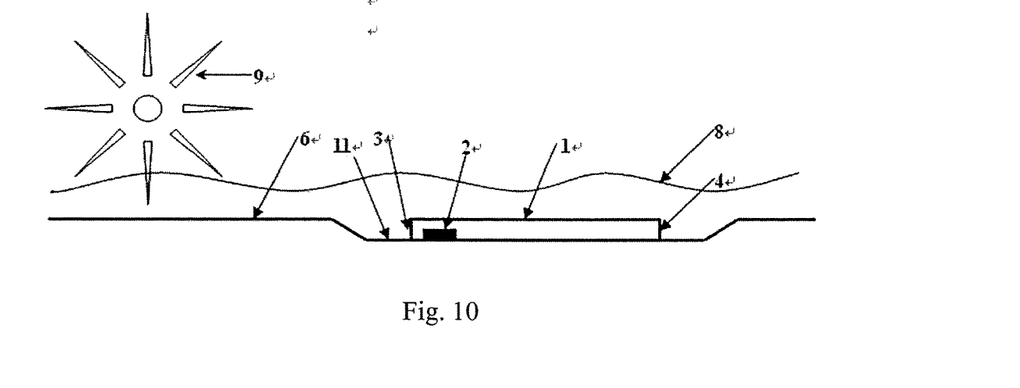
FIG. 10 is a side view of the carbon supplement device of the invention, which is mounted in a position lower than the bottom of the open pond.

When the depth of the culture solution in the open pond is relatively small, the stirrer 9 of the open pond can be arranged above an arc-shaped groove 10, and the blade tip of the stirrer is lower than the bottom of the open pond (FIG. 8); and a shallow groove 11 can be dug out in the region at the bottom of the open pond where the carbon supplement device is to be placed so as to install the carbon supplement device, namely the carbon supplement device is installed at a position lower than the bottom of the open pond (FIG. 9 and FIG. 10). The bottom of the shallow groove 11 for installing the carbon supplement device can be a flat bottom, a flat bottom with round corners or a semi-circular bottom (FIG. 9); and the material of the groove 11 can be cement, a plastic plate, a stainless steel plate, bricks, the same material as that of the bottom of the open pond or the like.

Embodiment 1

As shown in FIG. 11, *spirulina* is cultivated in a raceway type culture pond (a most common open pond, referred as a raceway pond), wherein the flow channel of the raceway pond has a perimeter of 70 m and a width of 3 m. A stirrer 9 comprises four groups of steel paddle wheels driven by a rotating shaft, each paddle wheel comprising four blades spaced by 90-degree, the blades of two adjacent paddle wheels are staggered by 45-degree, the rotating shaft being driven by an alternating current motor through variable gearing, and the radius of the stirrer 9 in rotating being 50 cm.

One group containing six horizontal submerged cover type carbon supplement devices is arranged in the raceway pond along the direction of the flow channel, and each horizontal submerged cover type carbon supplement device comprises a cover 1 along the flow direction of the culture solution and a gas distributor 2 shrouded by the cover 1. Each cover 1 is made of a stainless steel sheet with a thickness of 1 mm; the shape of cross-section of the main body of the cover 1 is semi-circular; and each cover 1 has a length of 400 cm, a width of 10 cm and a height of 5 cm. The gas distributor 2, a micro-porous rubber film aeration pipe with a length of 50 cm, an outer diameter of 16 mm, an inner diameter of 10 mm and a pore size of about 30-60 μm, is positioned in the region apart from the culture solution inlet 3 by 0-50 cm under the cover 1 along the flow direction of the culture solution and positioned centrally in the radial direction. The culture solution is driven by the stirrer 9 to flow along the raceway pond channel, such that part of the culture solution flows into the carbon supplement device from the culture solution inlet 3 so as to be in contact with the bubbles released from the gas distributor 2, then the culture solution flows through the space below the cover 1 till flows out of the culture solution outlet 4 of the carbon supplement device. Then, the culture solution out of the outlet 4 of the carbon supplement device is mixed with the culture solution which does not enter the carbon supplement device to flow in the flow channel.

Figure 12:
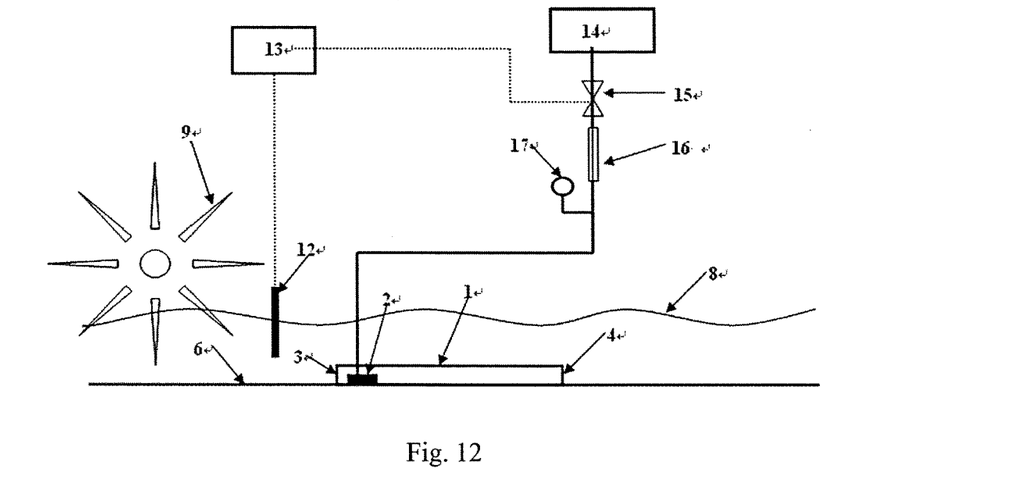
FIG. 12 is a schematic diagram of a system utilizing the carbon supplement device of the invention for automatic carbon supplement.

The carbon supplementing procedure is controlled in an automatic mode, such as the method disclosed in application with No. CN200410009360.4, and a system for implementing the control is shown in FIG. 12, wherein, a pH sensor 12 is a commercially available pH sensor, a control device 13 is a pH meter with a switch controller, a $CO_2$ gas source 14 is pure carbon dioxide gas from a steel cylinder, and an execution mechanism 15 is a two-position normally-closed solenoid valve (the flow diameter of the valve is 8 mm). The carbon dioxide delivering valve (the execution mechanism 15) is controlled to be open or closed according to the pH value of the culture solution. The flow rate and the pressure of $CO_2$ gas are monitored by a flow meter 16 and a pressure gauge 17.

The algae species is *Spirulina Platensis*, numbered 439, which is from the Freshwater Algae Culture Collection of the Institute of Hydrobiology, Chinese Academy of Sciences. The medium is Zarrouk medium, wherein the initial concentration of sodium bicarbonate is 0.05 mol/L. The average depth of the culture solution in the raceway pond is 15 cm, and the inoculation density of algae cells is 0.40 g (dry cell weight)/L. The range of the pH value of the culture solution is controlled within 9.6-9.7, and when the pH value of the culture solution rises to 9.6, automatic carbon supplementing procedure is initiated. The flow rate of the carbon dioxide gas of each gas distributor (while the execution mechanism 15 is open) is 1 L/min (pure carbon dioxide, standard conditions). The rotational speed of the motor is regulated to enable the flow velocity of the culture solution in the raceway pond to be about 25 cm/s.

The concentration of other nutrient salts is detected and supplemented timely if necessary every day, and a small amount of water is also supplemented to make up for the loss of water caused by evaporation. After the culture procedure is continuously carried on for 6 days, the density of the algae cells reaches 0.70 g (dry cell weight)/L, and the production of the algae cells per unit area reaches 13.3 g (dry cell weight)/m$^2$·d. The composition and the content of conventional components, amino acids, fatty acids and carotenoids of the obtained *spirulina* algae powder are basically consistent with those reported in prior art documents. From calculation according to material balance the utilization efficiency of the carbon dioxide from the steel cylinder reaches 92%.

Embodiment 2

The features that are the same as those of embodiment 1 are omitted. *Chlorella* sp. is cultivated in the open pond, and the medium is BG-11 medium with NaNO$_3$ as nitrogen source. The average depth of the culture solution in the raceway pond is 12 cm. The inoculation density of the algae cells is 0.5 g (dry cell weight)/L. The range of the pH value of the culture solution is controlled within 7.5-7.6. The flow rate of the carbon dioxide gas of each gas distributor (while the execution mechanism 15 is open) is 0.5 L/min (pure carbon dioxide, standard conditions). The flow velocity of the culture solution in the raceway pond is about 30 cm/s. After the culture procedure is continuously carried on for 6 days, the utilization efficiency of the carbon dioxide from the steel cylinder reaches 90%.

Embodiment 3

The features that are the same as those of embodiment 1 are omitted. In this embodiment, each cover has a length of 800 cm, a width of 6 cm and a height of 3 cm. The average depth of the culture solution in the raceway pond is 10 cm. The inoculation density of the algae cells is 0.6 g (dry cell weight)/L. The range of the pH value of the culture solution is controlled within 9.5-9.6. The flow rate of the carbon dioxide gas of each gas distributor (while the execution mechanism 15 is open) is 1 L/min (pure carbon dioxide, standard conditions). The flow velocity of the culture solution in the raceway pond is about 50 cm/s. After the culture procedure is continuously carried on for 6 days, the utilization efficiency of the carbon dioxide from the steel cylinder reaches 98%.

Embodiment 4

The features that are the same as those of embodiment 1 are omitted. One group containing three horizontal submerged cover type carbon supplement devices is arranged, each horizontal submerged cover type carbon supplement device comprises a cover along the flow direction of the culture solution and four gas distributors shrouded by the cover. The shape of cross-section of the main body of the cover is arc-shaped, with each cover having a length of 200 cm, a width of 40 cm and a height of 10 cm. *Chlorella* sp. is cultured in the open pond, wherein the medium is BG-11 medium with NaNO$_3$ as nitrogen source. The average depth of the culture solution in the raceway pond is 20 cm. The inoculation density of the algae cells is 0.3 g (dry cell weight)/L. The range of the pH value of the culture solution is controlled within 7.5-7.6. The flow rate of the carbon dioxide gas of each gas distributor (while the execution mechanism 15 is open) is 0.5 L/min (pure carbon dioxide, standard conditions). The flow velocity of the culture solution in the raceway pond is about 25 cm/s. After the culture procedure is continuously carried on for 6 days, the utilization efficiency of the carbon dioxide from the steel cylinder reaches 86%.

Embodiment 5

The features that are the same as those of embodiment 1 are omitted. A semi-circular arc-shaped groove with a radius of 52 cm and a depth of 10 cm is dug out below the stirrer to lower the blade tip of the stirrer to be 8 cm lower than the bottom of the raceway pond. Each horizontal submerged cover type carbon supplement device comprises a cover along the flow direction of the culture solution and two gas distributors shrouded by the cover. The shape of the cross-section of the main body of the cover is arc-shaped, with each cover having a length of 200 cm, a width of 15 cm and a height of 3 cm. A shallow groove with a depth of 2 cm and with a flat bottom and two slope sides is dug out at the bottom of the raceway pond in the region below each carbon supplement device, each of the cover and the gas distributors is mounted on the flat bottom of the shallow groove (FIG. 9 and FIG. 10). *Scenedesmus* sp. is cultivated in the open pond, wherein the medium is BG-11 medium with NaNO$_3$ as nitrogen source. The average depth of the culture solution in the raceway pond is 5 cm. The inoculation density of the algae cells is 1.2 g (dry cell weight)/L. The range of the pH value of the culture solution is controlled within 7.4-7.5. The flow rate of the carbon dioxide gas of each gas distributor (while the execution mechanism 15 is open) is 0.5 L/min (pure carbon dioxide, standard conditions). The flow velocity of the culture solution in the raceway pond is about 25 cm/s. After the culture procedure is continuously carried on for 6 days, the utilization efficiency of the carbon dioxide from the steel cylinder reaches 85%.

Embodiment 6

The features that are the same as those of embodiment 1 are omitted. A semi-circular arc-shaped groove with a radius of 52 cm and a depth of 10 cm is dug out below the stirrer to lower the blade tip of the stirrer to be 8 cm lower than the bottom of the raceway pond. Each horizontal submerged cover type carbon supplement device comprises a cover along the flow direction of the culture solution and two gas distributors shrouded by the cover. The shape of the cross-section of the main body of the cover is arc-shaped, with each cover having a length of 200 cm, a width of 10 cm and a height of 2 cm. A shallow groove with a depth of 3 cm and with a flat bottom and two slope sides, is dug out at the bottom of the raceway pond in the region below each carbon supplement device, and each of the cover and the gas distributors is mounted overhead by 1 cm over the flat bottom of the shallow groove (FIG. 9, FIG. 10 and FIG. 6). The average depth of the culture solution in the raceway pond is 3 cm. The inoculation density of the algae cells is 2 g (dry cell weight)/L. The range of the pH value of the culture solution is controlled within 9.7-9.8. The flow rate of the carbon dioxide gas of each gas distributor (while the execution mechanism 15 is open) is 0.5 L/min (pure carbon dioxide, standard conditions). The flow velocity of the culture solution in the raceway pond is about 25 cm/s. After the culture procedure is continuously carried on for 6 days, the utilization efficiency of the carbon dioxide from the steel cylinder reaches 88%.

Embodiment 7

The features that are the same as those of embodiment 1 are omitted. The shape of the cross-section of the main body of the cover is trapezoidal, with each cover having a length of 100 cm, a width of 15 cm and a height of 15 cm. The gas distributor, a variable-pore aeration hose with a diameter of 65 mm and a length of 40 cm, is positioned in the region apart from the culture solution inlet by 0-40 cm under the cover along the flow direction of the culture solution. The average depth of the culture solution in the raceway pond is 25 cm. The inoculation density of the algae cells is 0.24 g (dry cell weight)/L. The range of the pH value of the culture solution is controlled within 9.8-9.9. The flow rate of the carbon dioxide gas of each gas distributor (while the execution mechanism 15 is open) is 1 L/min (pure carbon dioxide, standard conditions). The flow velocity of the culture solution in the raceway pond is about 20 cm/s. After the culture procedure is continuously carried on for 6 days, the utilization efficiency of the carbon dioxide from the steel cylinder reaches 79%.

Embodiment 8

The features that are the same as those of embodiment 1 are omitted. Each horizontal submerged cover type carbon supplement device comprises a cover along the flow direction of the culture solution and two gas distributors shrouded by the cover. The shape of the cross-section of the main body of the cover is rectangular, with each cover having a length of 50 cm, a width of 20 cm and a height of 20 cm. The gas distributors are sand cores with a diameter of 30 mm and a height of 70 mm, which are arranged side by side vertically to the flow direction of the culture solution and apart from the culture solution inlet by 5-10 cm under the cover. The average depth of the culture solution in the raceway pond is 30 cm. The inoculation density of the algae cells is 0.2 g (dry cell weight)/L. The range of the pH value of the culture solution is controlled within 9.9-10.0. The flow rate of the carbon dioxide gas of each gas distributor (while the execution mechanism 15 is open) is 0.5 L/min (pure carbon dioxide, standard conditions). The flow velocity of the culture solution in the raceway pond is about 15 cm/s. After the culture procedure is continuously carried on for 6 days, the utilization efficiency of the carbon dioxide from the steel cylinder reaches 75%.

The invention claimed is:

1. A horizontal submerged cover type carbon supplement device for cultivating microalgae in an open pond, comprises: at least one cover and at least one gas distributor, wherein the at least one gas distributor is arranged at a bottom of the open pond and the at least one cover is arranged above the at least one gas distributor; the at least one cover, in a form of a cylinder with an opening at a first end and a second end thereof, is arranged along a flow direction of a culture solution, the first end of the at least one cover being a culture solution inlet and the second end of the at least one cover being a culture solution outlet and the top of the at least one cover being inundated by the culture solution; the at least one gas distributor being entirely positioned at least 40 cm from the culture solution outlet of the at least one cover.

2. The carbon supplement device according to claim 1, wherein a distance between the at least one gas distributor and the culture solution outlet of the at least one cover is between 60-750 cm.

3. The carbon supplement device according to claim 1, wherein the at least one cover is directly mounted at the bottom of the open pond or overhead arranged at the bottom of the open pond.

4. The carbon supplement device according to claim 1, wherein a bottom of the at least one cover is a closed structure.

5. The carbon supplement device according to claim 1, wherein a body of the at least one cover is one of a semi-circular cylinder, an arc-shaped cylinder, a rectangular cylinder and a trapezoidal cylinder.

6. The carbon supplement device according to claim 1, wherein the first and second ends of the at least one cover are formed with a bell mouth.

7. The carbon supplement device according to claim 1, wherein a height of the at least one cover is 2-20 cm.

8. The carbon supplement device according to claim 1, wherein a width of the at least one cover is at least 2 cm.

9. The carbon supplement device according to claim 1, wherein the carbon supplement device comprises at least two covers forming a conjoined structure.

10. A carbon supplement method for cultivating microalgae in an open pond based on the carbon supplement device of claim 1, comprises: the horizontal submerged cover type carbon supplement device is arranged at the bottom of the open pond along the direction of the channel of the open pond to enable the culture solution to inundate the top of the cover; the culture solution flows into the culture solution inlet of the cover under the driving of a stirrer of the open pond and flows out of the culture solution outlet of the cover after being in contact with $CO_2$ released from the gas distributor in the carbon supplement device;

the flow velocity of the culture solution in the open pond is 20-50 cm/s;

the flow rate of the $CO_2$ in the horizontal submerged type carbon supplement device, calculated as pure $CO_2$ under standard condition, is 0.1-20 L/min per meter of the width of the open pond.

11. The carbon supplement method according to claim 10, wherein the depth of the culture solution in the open pond is 2-30 cm.

12. The carbon supplement method according to claim 10, wherein the blade tip of the stirrer is lower than the bottom of the open pond.

13. The carbon supplement method according to claim 10, wherein the horizontal submerged cover type carbon supplement device is arranged in a shallow groove at the bottom of the open pond.

14. The carbon supplement method according to claim 10, wherein the bottom of the shallow groove is a flat bottom, a flat bottom with round corners or a semi-circular bottom.

15. The carbon supplement method according to claim 10, wherein the $CO_2$ is one or more of cleaned flue gas, industrial $CO_2$ gas, pure $CO_2$ gas or air mixed with $CO_2$, or liquid $CO_2$.

16. The carbon supplement method according to claim 10, wherein the medium for cultivating microalgae is Zarrouk medium, SM medium, ASP2 medium or BG-11 medium.

17. The carbon supplement method according to claim 10, wherein the microalgae are *spirulina, scenedesmus, haematococcus pluvialis, Dunaliella salina, chlorella*, or *chlamydomonas*.

* * * * *